United States Patent [19]
Fletcher

[11] Patent Number: 6,030,217
[45] Date of Patent: Feb. 29, 2000

[54] JAW RETENTION DEVICE

[76] Inventor: Thomas G. Fletcher, 2161 South Downing, Denver, Colo. 80210

[21] Appl. No.: 08/866,186

[22] Filed: May 30, 1997

[51] Int. Cl.[7] ............................................. A61C 5/00
[52] U.S. Cl. .......................... 433/140; 600/206; 600/237
[58] Field of Search ................................. 433/229, 140, 433/137; 600/201, 206, 210, 213, 215, 217, 226, 237, 238, 239, 242; 24/300, 301

[56] References Cited

U.S. PATENT DOCUMENTS

| | | | |
|---|---|---|---|
| 160,604 | 3/1875 | Lewis | 433/137 |
| 649,854 | 5/1900 | Lundborg | 600/242 |
| 785,529 | 3/1905 | Thomson | 600/238 |
| 1,009,551 | 11/1911 | Nations | 600/242 |
| 1,400,854 | 12/1921 | Barr | 600/242 |
| 2,575,204 | 11/1951 | Brown . | |
| 2,704,071 | 3/1955 | Becker . | |
| 3,290,743 | 12/1966 | Hanson . | |
| 3,542,015 | 11/1970 | Steinman | 600/206 |
| 4,259,068 | 3/1981 | Stephens | 433/140 |
| 4,569,108 | 2/1986 | Schwab . | |
| 4,831,697 | 5/1989 | Chuan . | |
| 5,462,435 | 10/1995 | Young | 433/140 |
| 5,514,076 | 5/1996 | Ley | 600/206 |
| 5,558,622 | 9/1996 | Greenberg | 600/237 |
| 5,638,584 | 6/1997 | De Anfrasio . | |
| 5,845,370 | 12/1998 | Cohoon . | |

FOREIGN PATENT DOCUMENTS

| | | | |
|---|---|---|---|
| 284937 | 1/1953 | Switzerland | 600/242 |
| 509419 | 7/1937 | United Kingdom | 600/242 |

*Primary Examiner*—Ralph A. Lewis
*Attorney, Agent, or Firm*—Timothy J. Martin; Michael R. Henson; Mark H. Weygandt

[57] ABSTRACT

A jaw retention device operative for use by a dental patient to urge the patient's lower jaw into an open position thereby relieving stress on the jaw muscles during dental procedures. The device includes a hand held object connected by an elongated flexible member to a mouth piece. The mouth piece is preferably constructed of a plastic material having sufficient flexibility to permit the mouth piece to bend and release from the lower teeth when the flexible member is subjected to a selected threshold tension.

17 Claims, 2 Drawing Sheets

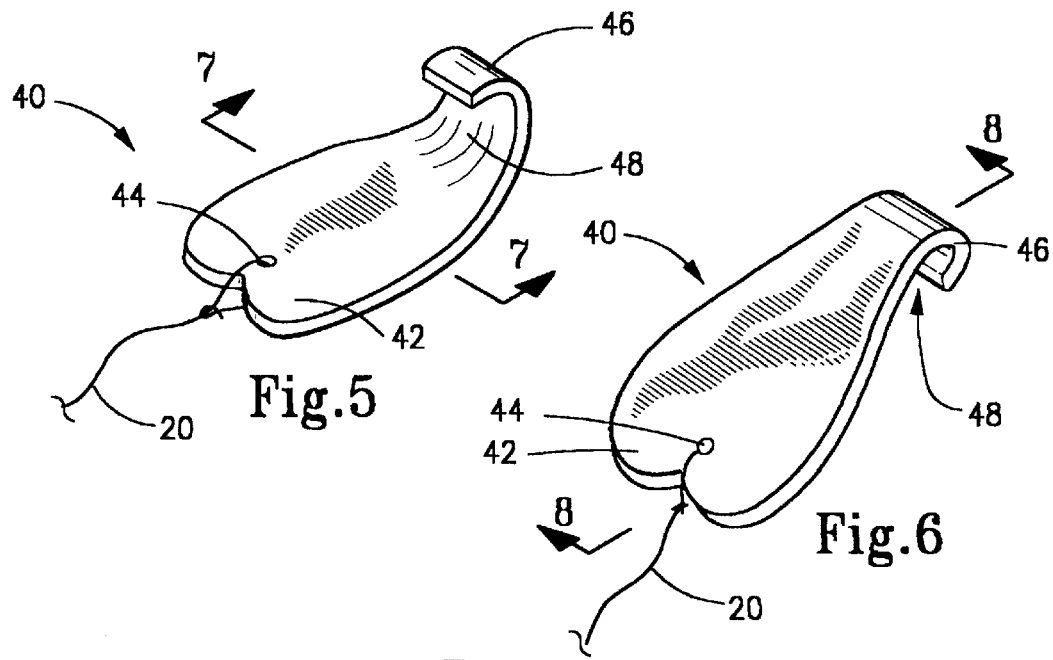
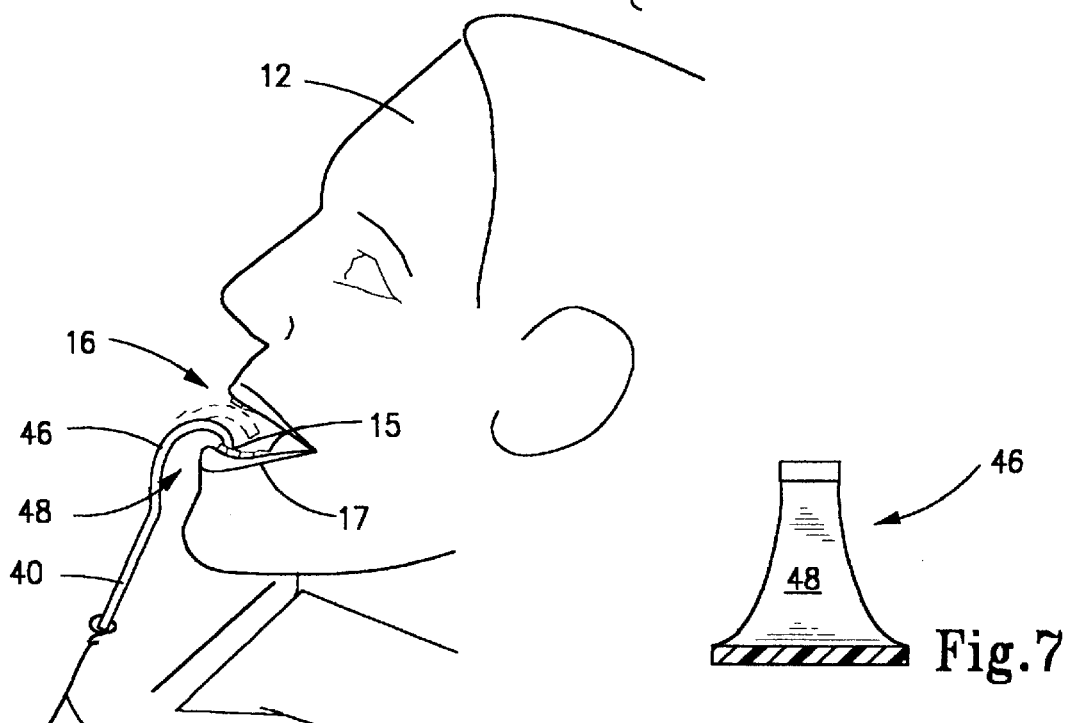
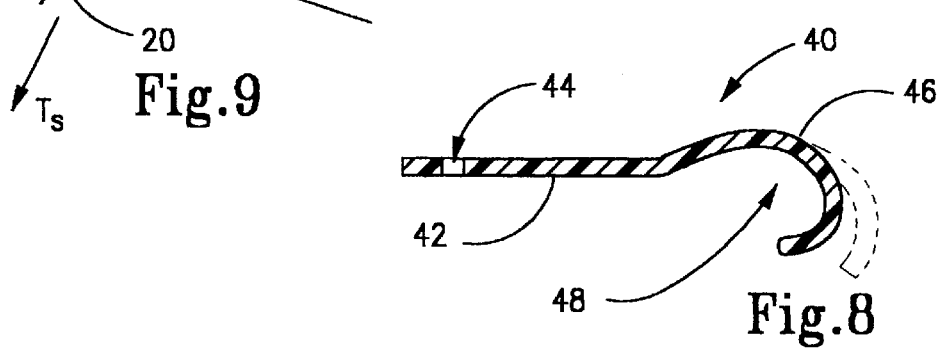

JAW RETENTION DEVICE

FIELD OF INVENTION

The present invention is broadly directed to implements for use in dental offices. More particularly, the present invention concerns jaw retention devices operative for use by patients to urge the patient's jaw into an open position, thereby to relieve stress on the jaw muscles during dental procedures.

BACKGROUND OF THE INVENTION

A dental appointment is rarely regarded as an enjoyable experience. Irrespective of whether one visits the dentist for a routine check-up such as a teeth cleaning or a more complicated procedure, the experience is often dreaded. This sentiment is shared by many adults and children alike who tend to view dental appointments as a mild form of torture, featuring medical instruments such as probes, forceps, pliers and drills.

In order to alleviate these anxieties, dentists, hygentists and other dental-care professionals do their best to relieve the nagging sense of general discomfort patients feel. These days, dentists will try just about anything to ease a patient's pain and distract the patient from the procedure at hand, including performing magic tricks. Industry professionals are also exploring ways of performing more comfortable procedures which require less intimidating medical instruments.

Throughout most of the duration of one's visit in the dental chair, it is necessary for the patient to keep his/her mouth in an open position to permit the dentist to have access to the patient's teeth. This can become quite an arduous task during prolonged dental procedures. In the past, dentists have employed rubber inserts which are wedged between the patient's upper and lower rows of teeth to force the mouth open. Until removal or repositioning of the inserts, however, the patient is unable to close his/her mouth, even when the dentist isn't working on the patient's teeth. The patient begins to feel helpless due to this lack of control over jaw movement. This is often psychologically distressing.

It is also not uncommon for the patient's jaws to become quite sore as a result of muscle stress which is exacerbated by the patient's tendency to clench the jaws while dental work is being performed. This is in part derived from the fact that jaw muscles are bio-functional for having strength in closing the mouth as opposed to opening the mouth. Inevitably, the patient's mouth has a tendency to return to its normally closed position to relieve stress on the jaw muscles for over-extended periods of opening. Unfortunately, this interferes with the dentist's access to the patient's mouth and can complicate the dental procedure or even result in unnecessary injury to the patient.

To date there are no known devices which assist the patient in controlling the open position of his/her jaw during dental work. Accordingly, there remains a need to provide such a device which accomplishes this and which also provides a source of distraction for the patient during dental work. The present invention is directed to meeting these needs, among others.

SUMMARY OF THE INVENTION

It is an object of the present invention to provide a new and useful jaw retention device which is operative for use by an individual to urge the individual's jaw into an open position.

It is another object of the present invention to provide a new and useful jaw retention device for use by dental patients to relieve muscle stress on the patient's jaw while dental work is being performed.

A further object of the present invention is to provide such a jaw retention device which does not substantially interfere with a dentist's ability to perform dental work on the patient.

Still a further object of the present invention is to provide a new and useful jaw retention device which provides a source of distraction for a dental patient, particularly a young child, during dental work.

It is also an object of the present invention to provide a new and useful jaw retention device which allows the patient to control jaw movement during dental procedures, both for physical reasons and for psychological comfort.

Yet another object of the present invention is to provide a jaw retention device which is inexpensive and easy to manufacture.

In accordance with these objectives, the present invention provides a jaw retention device which is operative for use by an individual to urge the individual's jaw into an open position. The jaw retention device is particularly adapted for use by dental patients of all ages and broadly comprises an elongated flexible member, a handhold object and a mouth piece. The elongated, flexible member has opposed first and second ends. The handhold object is disposed on the first end and is sized and adapted to be grasped by the individual. The mouth piece is disposed on the second end of the flexible member and this mouth piece includes an anchor portion which is sized for insertion into the individual's mouth. The anchor portion is further adapted to engage the individual's lower teeth so that when tension is placed on the flexible member, the individual's jaw is urged into the open position.

The mouth piece is preferably constructed of a material, such as plastic, having sufficient flexibility to permit the mouth piece to bend and release from the lower teeth when the flexible member is subjected to a selected threshold tension. The mouth piece includes a flattened portion attachable to the flexible member and the anchor portion is formed integrally with this flattened portion. The anchor portion defines a lip receiving recess which is sized and adapted to comfortably receive the patient's lower lip when the mouth piece is inserted into the patient's mouth. The lip recess may be lined with a cushion material, if desired.

The elongated member is releasably connectable to the mouth piece. One way of accomplishing this is by a hole formed in the mouth piece through which the flexible member is received. Preferably, the flexible member is selectively adjustable in length and may be constructed from a variety of materials, such as elastic. The flexible member is also releasably connectable to the handhold object and this handhold object may take on a variety of forms, such as toys or annular members. Alternatively, the handhold object could be formed by a looped portion of the flexible member's first end.

These and other objects of the present invention will become more readily appreciated and understood from a consideration of the following detailed description of the exemplary embodiments of the present invention when taken together with the accompanying drawings in which:

BRIEF DESCRIPTION OF THE DRAWINGS

FIG. 5 is a perspective view showing a preferred construction for the mouth piece depicted in FIGS. 1–4;

FIG. 6 is another perspective view showing the construction of the mouth piece;

FIG. 7 is a cross-sectional view of the mouth piece as seen about lines 7—7 in FIG. 5;

FIG. 8 is a sideview in cross-section showing the mouth piece as viewed about lines 8—8 in FIG. 6 and illustrating the ability of the mouth piece to flex; and FIG. 9 is a sideview in elevation showing the mouth piece inserted into a patient's mouth to engage the patient's teeth.

DETAILED DESCRIPTION OF THE EXEMPLARY EMBODIMENTS

The jaw retention device of the present invention is operative for use by an individual to urge the individual's jaw into an open position. The jaw retention device is particularly adapted for use by dental patients to relieve stress on the patient's jaw muscles during dental work. For younger patients the jaw retention device of the present invention also provides a source of amusement and distraction to alleviate some of the apprehension associated with visits to the dentist.

Figure 1:
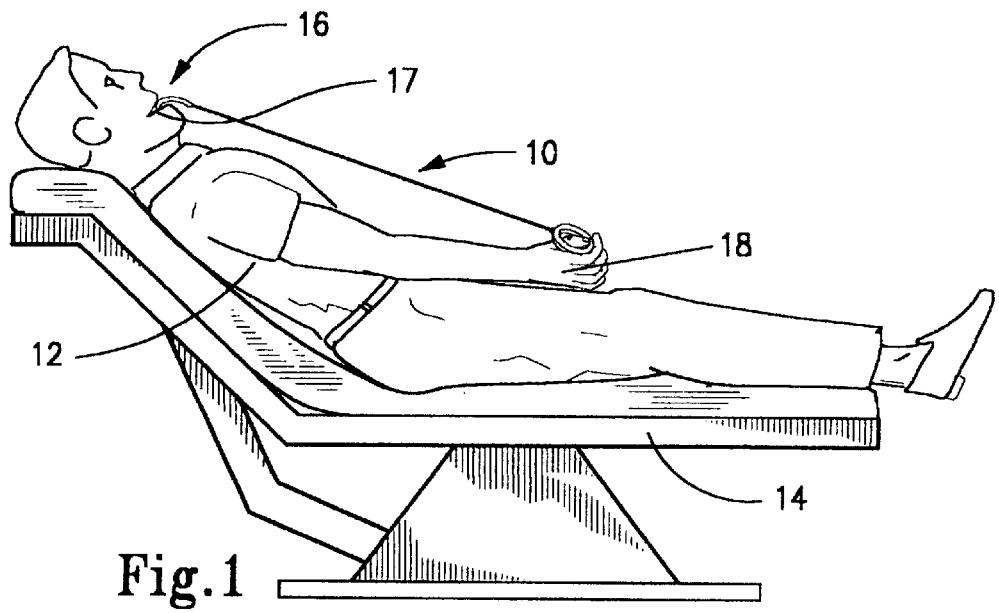
FIG. 1 is a sideview in elevation of a patient supported in a reclined position in a dentist's chair and showing the patient employing the jaw retention device according to the present invention to urge the patient's jaw into an open position.

FIG. 1 shows the jaw retention device 10 of the present invention employed by a patient 12 supported in a reclined position on a dental chair 14. More specifically, jaw retention device 10 is adapted to be inserted into the patient's mouth 16 and grasped by the patient's hand 18 to urge the patient's jaw 17 into an open position.

Figure 2:
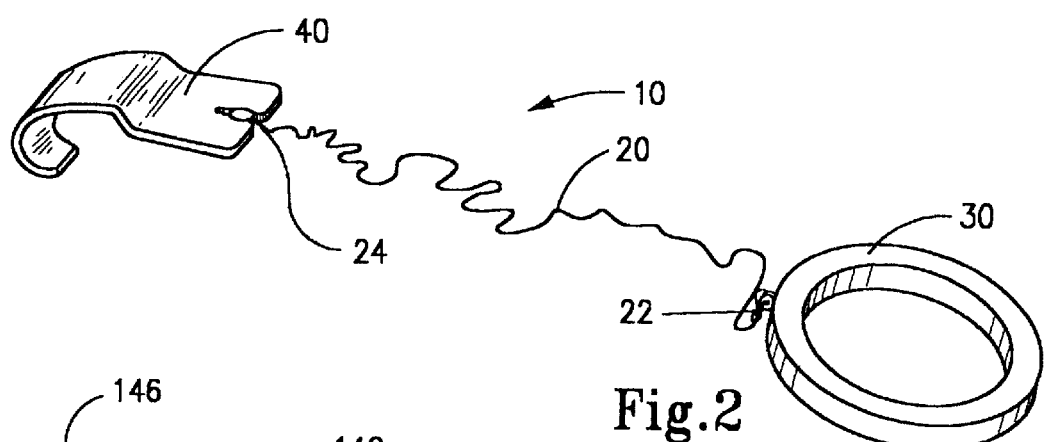
FIG. 2 is an enlarged perspective view of the jaw retention device shown in FIG. 1 according to a first exemplary embodiment of the present invention.

A first exemplary construction of the jaw retention device may be appreciated with reference to FIG. 2. Jaw retention device 10 broadly includes an elongated member 20, a handhold object 30 and a mouth piece 40. Flexible member 20 has a first end 22 and an opposite second end 24. Handhold object 30 is connected to first end 22 and is sized and adapted to be grasped by patient 12 during use of jaw retention device 10. Mouth piece 40 is disposed on second end 24 and is sized for insertion into the patient's mouth so that when flexible member 20 is pulled taut, the patient's jaw 16 is urged into the open position, as shown in FIG. 1.

Flexible member 20 can be selectably adjustable in length and it is preferred that it be releasably connectable to both handhold object 30 and mouthpiece 40. To this end, flexible member 20 may be constructed of an elastic material which is tied to both handhold object 30 and mouth piece 40 as shown in FIG. 2. Alternatively, of course, flexible member 20 may be a string or the like which is secured to handhold object 30 and mouth piece 40 through a variety of means known in the art.

Handhold object 30 may be in the form of an annular member as shown in FIG. 2. It should be appreciated, though, that the handhold object could also take on a variety of forms. For example, and as shown in FIG. 3, handhold object could be in the form of a toy truck 30, thereby to provide a source of distraction and amusement for younger dental patients during their visit to the dentist's office.

Figure 4:
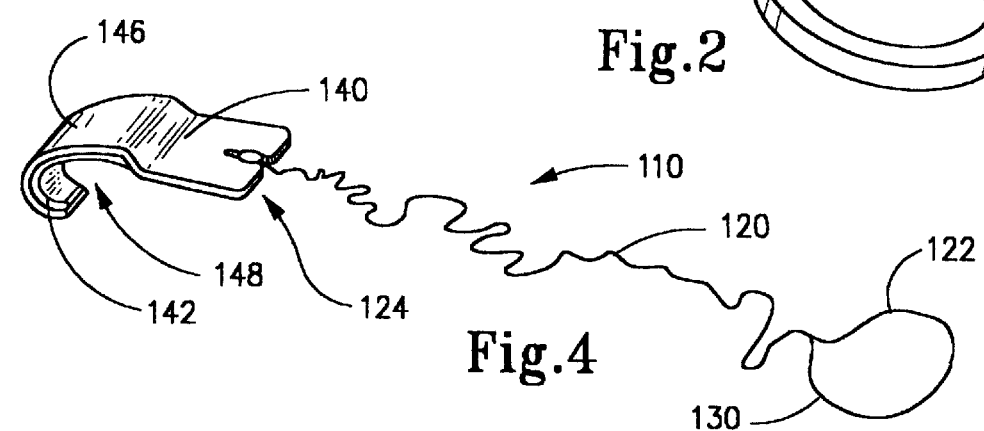
FIG. 4 is a perspective view showing a second exemplary embodiment for the jaw retention device of the present invention.

FIG. 4 shows a second exemplary construction for the jaw retention device of the present invention.

Here, jaw retention device 110 again includes an elongated, flexible member 120, handhold object 130 and mouth piece 140. Mouth piece 140 is releasably connectable to the second end 124 of flexible member 120. With this construction, however, handhold object 130 is actually formed by configuring a first end portion 122 of flexible member 120 into a loop which is sized to be grasped by the patient. This, of course, can be accomplished in a variety of ways, such as by tying or adhering segments of elongated member 120 together.

Figure 3:
FIG. 3 is a sideview in elevation showing an alternative construction for the handhold object for use with the jaw retention device according to the first exemplary embodiment of the present invention.

An exemplary construction for the mouth piece which may be utilized with any of the embodiments shown in FIGS. 2–4 is best appreciated with reference now to FIGS. 5–8. Mouth piece 40 preferably includes a flattened portion 42 which is releasably attachable to flexible member 20. A hole 44 may be formed in flattened portion 42 with flexible member 20 threadably received through hole 44. An anchor portion 46 is formed integrally with flattened portion 42. Anchor portion 46 is arcuate in configuration to define a lip receiving recess 48 which is sized and adapted to comfortably fit the patient's lip without stressing the lip when mouth piece 40 is inserted into the patient's mouth. Mouth piece 40 is preferably tapered in construction whereby flattened portion 42 is wider than anchor portion 46. As such, flattened portion 44 can be easily grasped by the patient when mouth piece 40 is inserted into the patient's mouth. Moreover, anchor portion 46 is sufficiently narrow so that it can adequately engage the patient's lower teeth while not substantially interfering with the dentist's access to the patient's mouth.

As shown in FIG. 8, mouth piece 40 is preferably constructed of a stiff yet resilient material to allow it to flex beyond its normal position. The advantage of this flexibility may be appreciated with reference to FIG. 9. When inserted into the patient's mouth 16, anchor portion 46 engages the patient's lower row of teeth 15 so that, when a selected tension is placed on flexible member 20 by patient 12, the patient's jaw 17 is urged into the open position. However, in the event an excessive amount of tension is applied to flexible member 20, as denoted by threshold tension "$T_s$" in FIG. 9, mouth piece 40, and specifically anchor portion 46, bends away from its normal position to release from lower teeth 15.

With reference again to FIG. 4, it may be appreciated that the lip recess may be lined with a cushioning material or a material that is of reduced sensitivity to patients. In FIG. 4, cushion liner 142 is shown in lip recess 148 of anchor portion 146. It should be understood that this liner 142 is secured in any convenient manner, i.e., an adhesive. Cushion liner 142 can be a thin foam rubber pad, soft plastic, etc.

With the above description in mind relating to the exemplary embodiments for the jaw retention device of the present invention, the ability of the jaw device to maintain a patient's jaw in an open position should now be readily appreciated. In use, the mouth piece is inserted into the patient's mouth so that the mouth piece's anchor portion engages the patient's lower row of teeth in such a manner that the patient's lip is placed against the mouth piece's lip recess region. The patient then grasps the handhold object and places a selected amount of tension on the flexible member in order to urge the patient's jaw into an open position, thereby relieving stress on jaw muscles. If the patient pulls too hard on the handhold object, however, a selected threshold tension is reached in the flexible member which causes the anchor portion of the mouth piece to bend and release from the lower teeth. This reduces the risk of injury to the patient during dental work. It should also be appreciated that the jaw retention device allows for mobility in that the mouthpiece thereof may be easily repositioned in the patient's mouth as the need arises.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. A jaw retention device operative for use by an individual to urge the individual's jaw into an open position, comprising:

(a) an elongated and collapsible flexible member having a first end and an opposite second end;

(b) a handhold object disposed on said first end, said handhold object sized and adapted to be grasped by the individual; and (c) a mouth piece disposed on said second end, said mouth piece including an anchor portion which is sized and adapted for insertion into the individual's mouth to anchor against the individual's jaw whereby tension placed on said flexible member urges the individual's jaw into the open position, said mouth piece constructed entirely of a plastic material that is flexible yet resilient so that said mouth piece is operative to bend and release from the individual's lower teeth when the flexible member is subjected to a selected threshold tension.

2. A jaw retention device according to claim 1 wherein said anchor portion is formed to included a lip receiving recess which is sized and adapted to comfortably receive the individual's lower lip when said mouth piece is inserted into the individual's mouth, and including a liner disposed on said anchor portion in the lip receiving recess.

3. A jaw retention device according to claim 1 wherein said flexible member is releasably connectable to said mouthpiece.

4. A jaw retention device according to claim 1 wherein said flexible member is releasably connectable to said handhold object.

5. A jaw retention device according to claim 1 wherein said handhold object is an annular member.

6. A jaw retention device according to claim 1 wherein said mouth piece includes a hole formed therein and through which said flexible member is received.

7. A jaw retention device according to claim 1 wherein said elongated, flexible member is constructed entirely of elastic material.

8. A jaw retention device according to claim 1 wherein said handhold object is fastened to said elongated, flexible member.

9. A jaw retention device according to claim 1 wherein said flexible member is a string.

10. A jaw retention device according to claim 9 wherein said handhold object is a looped portion of the string.

11. A jaw retention device according to claim 1 wherein said mouth piece includes a flattened portion formed integrally with said anchor portion, and wherein said mouth piece continuously tapers from said flattened portion toward an end of said anchor portion end so that said flattened portion in wider than said anchor portion.

12. A jaw retention device operative for use by an individual to urge the individual's jaw into an open position, comprising:

(a) an elongated flexible member having opposed first and second ends, there being a handhold object associated with said first end; and (b) a mouth piece connected to said second end and including an anchor portion and a flattened portion formed integrally with one another, said flattened portion secured to said flexible member and being formed to included a continuous and uninterrupted flat surface which spans an entire width of said flattened portion so that said flattened portion can be conveniently grasped be the individual, said anchor portion formed as an arcuate extension of said flat surface and being sized and adapted for insertion into the individual's mouth to anchor against the individual's lower teeth whereby tension placed on said flexible member urges the individual's law into the open position.

13. A jaw retention device according to claim 12 wherein said mouth piece is constructed entirely of plastic.

14. A jaw retention device according to claim 12 wherein said handhold object is selected from a group consisting of toys, annular members, and looped portions of said second end.

15. A jaw retention device according to claim 12 wherein said flexible member is constructed entirely of elastic material.

16. A jaw retention device according to claim 12 wherein said mouth piece continuously tapers from said flattened portion toward an end of said anchor portion end so that said flattened portion in wider than said anchor portion.

17. A jaw retention device according to claim 12 wherein said flexible member is a string.

* * * * *